US010430043B2

(12) United States Patent
Rosinko et al.

(10) Patent No.: US 10,430,043 B2
(45) Date of Patent: *Oct. 1, 2019

(54) PREVENTING INADVERTENT CHANGES IN AMBULATORY MEDICAL DEVICES

(71) Applicant: Tandem Diabetes Care, Inc., San Diego, CA (US)

(72) Inventors: Michael Rosinko, Anaheim, CA (US); Geoff Kruse, San Diego, CA (US); Thomas Ulrich, San Diego, CA (US); Erik Verhoef, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 84 days.

This patent is subject to a terminal disclaimer.

(21) Appl. No.: 15/592,595

(22) Filed: May 11, 2017

(65) Prior Publication Data

US 2017/0300206 A1 Oct. 19, 2017

Related U.S. Application Data

(63) Continuation of application No. 13/801,230, filed on Mar. 13, 2013, now Pat. No. 9,715,327.

(Continued)

(51) Int. Cl.
*G06F 19/00* (2018.01)
*G06F 3/0484* (2013.01)
(Continued)

(52) U.S. Cl.
CPC ........ *G06F 3/0484* (2013.01); *G06F 19/3468* (2013.01); *G16H 20/17* (2018.01); *G16H 40/63* (2018.01); *A61M 5/14* (2013.01)

(58) Field of Classification Search
CPC .. G06F 19/3468; G06F 3/0481; G06F 3/0482; G06F 3/0484; G06F 3/04842;
(Continued)

(56) References Cited

U.S. PATENT DOCUMENTS

| 4,191,184 A | 3/1980 | Carlisle |
| 4,810,243 A | 3/1989 | Howson |

(Continued)

FOREIGN PATENT DOCUMENTS

| EP | 0985420 A2 | 3/2000 |
| EP | 1769812 A1 | 4/2007 |

(Continued)

OTHER PUBLICATIONS

US 8,333,733 B2, 12/2012, Lanigan et al. (withdrawn)

(Continued)

*Primary Examiner* — Rinna Yi
(74) *Attorney, Agent, or Firm* — Patterson Thuente Pedersen, P.A.

(57) ABSTRACT

A portable medical device is operated in an active mode in which the device receives a user input at an input interface and provides the received user input to a processor of the device. The active mode is terminated and the device is operated in a safe mode, in which the received user input is not provided to the processor and/or one or more device function is disabled, in response to determining that the received user input was received in an out of bounds region of the input interface. The safe mode is terminated in response to receiving a predetermined user input comprising an activation input.

18 Claims, 7 Drawing Sheets

Related U.S. Application Data

(60) Provisional application No. 61/656,997, filed on Jun. 7, 2012.

(51) Int. Cl.
  *G16H 20/17* (2018.01)
  *G16H 40/63* (2018.01)
  *A61M 5/14* (2006.01)

(58) Field of Classification Search
  CPC .... G06F 3/04847; G06F 3/0488; A61M 5/14; A61M 1/02; A61M 5/142; A61M 5/14244; A61M 2205/3569
  See application file for complete search history.

(56) References Cited

U.S. PATENT DOCUMENTS

| | | |
|---|---|---|
| 5,207,666 A | 5/1993 | Idriss et al. |
| 5,247,434 A | 9/1993 | Peterson et al. |
| 5,338,157 A | 8/1994 | Blomquist |
| 5,438,510 A | 8/1995 | Bryant et al. |
| 5,485,408 A | 1/1996 | Blomquist |
| 5,497,772 A | 3/1996 | Schulman et al. |
| 5,498,421 A | 3/1996 | Grinstaff et al. |
| 5,558,638 A | 9/1996 | Evers et al. |
| 5,582,593 A | 12/1996 | Hultman |
| 5,634,896 A | 6/1997 | Bryant et al. |
| 5,639,473 A | 6/1997 | Grinstaff et al. |
| 5,660,163 A | 8/1997 | Schulman et al. |
| 5,681,285 A | 10/1997 | Ford et al. |
| 5,685,844 A | 11/1997 | Marttila |
| 5,707,212 A | 1/1998 | Matthews |
| 5,728,396 A | 3/1998 | Peery et al. |
| 5,782,805 A | 7/1998 | Meinzer et al. |
| 5,830,195 A | 11/1998 | Peters et al. |
| 5,848,593 A | 12/1998 | McGrady et al. |
| 5,935,099 A | 8/1999 | Peterson et al. |
| 5,964,724 A | 10/1999 | Rivera et al. |
| 5,985,305 A | 11/1999 | Peery et al. |
| 5,988,851 A | 11/1999 | Gent |
| 6,024,539 A | 2/2000 | Blomquist |
| 6,056,522 A | 5/2000 | Johnson |
| 6,070,761 A | 6/2000 | Bloom et al. |
| 6,126,642 A | 10/2000 | Kriesel et al. |
| 6,198,383 B1 | 3/2001 | Sekura et al. |
| 6,241,704 B1 | 6/2001 | Peterson et al. |
| 6,269,340 B1 | 7/2001 | Ford et al. |
| 6,395,292 B2 | 5/2002 | Peery et al. |
| 6,425,878 B1 | 7/2002 | Shekalim |
| 6,427,088 B1 | 7/2002 | Bowman, IV et al. |
| 6,470,234 B1 | 10/2002 | McGrady |
| 6,475,180 B2 | 11/2002 | Peterson et al. |
| 6,511,435 B1 | 1/2003 | Bluth et al. |
| 6,537,272 B2 | 3/2003 | Christopherson et al. |
| 6,551,276 B1 | 4/2003 | Mann et al. |
| 6,554,798 B1 | 4/2003 | Mann et al. |
| 6,562,001 B2 | 5/2003 | Lebel et al. |
| 6,564,105 B2 | 5/2003 | Starkweather et al. |
| 6,571,128 B2 | 5/2003 | Lebel et al. |
| 6,577,899 B2 | 6/2003 | Lebel et al. |
| 6,585,644 B2 | 7/2003 | Lebel et al. |
| 6,635,014 B2 | 10/2003 | Starkweather et al. |
| 6,635,048 B1 | 10/2003 | Ullestad et al. |
| 6,648,821 B2 | 11/2003 | Lebel et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,694,191 B2 | 2/2004 | Starkweather et al. |
| 6,733,446 B2 | 5/2004 | Lebel et al. |
| 6,738,052 B1 | 5/2004 | Manke et al. |
| 6,740,075 B2 | 5/2004 | Lebel et al. |
| 6,744,350 B2 | 6/2004 | Blomquist |
| 6,758,810 B2 | 7/2004 | Lebel et al. |
| 6,759,386 B2 | 7/2004 | Franco |
| 6,783,328 B2 | 8/2004 | Lucke et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,852,104 B2 | 2/2005 | Blomquist |
| 6,872,200 B2 | 3/2005 | Mann et al. |
| 6,873,268 B2 | 3/2005 | Lebel et al. |
| 6,936,029 B2 | 8/2005 | Mann et al. |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,979,326 B2 | 12/2005 | Mann et al. |
| 6,990,809 B2 | 1/2006 | Abouraphael |
| 6,997,920 B2 | 2/2006 | Mann et al. |
| 7,024,245 B2 | 4/2006 | Lebel et al. |
| 7,025,743 B2 | 4/2006 | Mann et al. |
| 7,090,648 B2 | 8/2006 | Sackner et al. |
| 7,091,179 B2 | 8/2006 | Franco |
| 7,109,878 B2 | 9/2006 | Mann et al. |
| 7,118,676 B2 | 10/2006 | Mueth et al. |
| 7,141,425 B2 | 11/2006 | Dzekunov et al. |
| 7,153,823 B2 | 12/2006 | Franco |
| 7,166,280 B2 | 1/2007 | Franco |
| 7,171,274 B2 | 1/2007 | Starkweather et al. |
| 7,201,730 B2 | 4/2007 | Davidner et al. |
| 7,204,823 B2 | 4/2007 | Estes et al. |
| 7,207,964 B2 | 4/2007 | Davidner et al. |
| 7,256,771 B2 | 8/2007 | Novak et al. |
| 7,256,888 B2 | 8/2007 | Staehr et al. |
| 7,264,730 B2 | 9/2007 | Connell et al. |
| 7,303,680 B2 | 12/2007 | Connell et al. |
| 7,318,892 B2 | 1/2008 | Connell et al. |
| 7,347,819 B2 | 3/2008 | Lebel et al. |
| 7,347,836 B2 | 3/2008 | Peterson et al. |
| 7,351,340 B2 | 4/2008 | Connell et al. |
| 7,369,635 B2 | 5/2008 | Spital et al. |
| 7,390,314 B2 | 6/2008 | Stutz, Jr. et al. |
| 7,445,616 B2 | 11/2008 | Petrakis |
| 7,455,663 B2 | 11/2008 | Bikovsky |
| 7,471,994 B2 | 12/2008 | Ford et al. |
| 7,514,401 B2 | 4/2009 | Franco |
| 7,515,060 B2 | 4/2009 | Blomquist |
| 7,591,801 B2 | 9/2009 | Brauker et al. |
| 7,594,889 B2 | 9/2009 | St. Ores et al. |
| 7,630,791 B2 | 12/2009 | Nguyen et al. |
| 7,651,489 B2 | 1/2010 | Estes et al. |
| 7,654,976 B2 | 2/2010 | Peterson et al. |
| 7,657,313 B2 | 2/2010 | Rom |
| 7,678,071 B2 | 3/2010 | Lebel et al. |
| 7,682,338 B2 | 3/2010 | Griffin |
| 7,699,767 B2 | 4/2010 | Mueth et al. |
| 7,713,574 B2 | 5/2010 | Brister et al. |
| 7,717,903 B2 | 5/2010 | Estes et al. |
| 7,736,338 B2 | 6/2010 | Kavazov et al. |
| 7,774,145 B2 | 8/2010 | Brauker et al. |
| 7,778,680 B2 | 8/2010 | Goode, Jr. et al. |
| 7,789,857 B2 | 9/2010 | Moberg et al. |
| 7,797,028 B2 | 9/2010 | Goode, Jr. et al. |
| 7,801,596 B2 | 9/2010 | Fischell et al. |
| 7,811,279 B2 | 10/2010 | John |
| 7,815,602 B2 | 10/2010 | Mann et al. |
| 7,819,843 B2 | 10/2010 | Mann et al. |
| 7,828,528 B2 | 11/2010 | Estes et al. |
| 7,831,310 B2 | 11/2010 | Lebel et al. |
| 7,837,647 B2 | 11/2010 | Estes et al. |
| 7,837,651 B2 | 11/2010 | Bishop et al. |
| 7,875,022 B2 | 1/2011 | Wenger et al. |
| 7,912,674 B2 | 3/2011 | Killoren et al. |
| 7,914,450 B2 | 3/2011 | Goode, Jr. et al. |
| 7,925,321 B2 | 4/2011 | Goode et al. |
| 7,933,639 B2 | 4/2011 | Goode et al. |
| 7,933,780 B2 | 4/2011 | De La Huerga |
| 7,935,074 B2 | 5/2011 | Plahey et al. |
| 7,938,792 B2 | 5/2011 | Roger et al. |
| 7,945,452 B2 | 5/2011 | Fathallah et al. |
| 7,955,261 B2 | 6/2011 | Goode et al. |
| 7,957,984 B1 | 6/2011 | Vallone |
| 7,959,569 B2 | 6/2011 | Goode et al. |

(56) References Cited

U.S. PATENT DOCUMENTS

| | | |
|---|---|---|
| 7,959,608 B2 | 6/2011 | Nash et al. |
| 7,963,954 B2 | 6/2011 | Kavazov |
| 7,972,296 B2 | 7/2011 | Braig et al. |
| 7,976,492 B2 | 7/2011 | Brauker et al. |
| 7,976,530 B2 | 7/2011 | Johnson et al. |
| 7,976,778 B2 | 7/2011 | Drucker et al. |
| 7,979,104 B2 | 7/2011 | Kamath et al. |
| 7,986,986 B2 | 7/2011 | Goode et al. |
| 7,988,674 B2 | 8/2011 | Adams et al. |
| 7,988,849 B2 | 8/2011 | Biewer et al. |
| 8,002,700 B2 | 8/2011 | Ferek-Petric et al. |
| 8,012,119 B2 | 9/2011 | Estes et al. |
| 8,020,564 B2 | 9/2011 | Batch |
| 8,034,019 B2 | 10/2011 | Nair et al. |
| 8,034,026 B2 | 10/2011 | Grant et al. |
| 8,052,601 B2 | 11/2011 | Goode, Jr. et al. |
| 8,066,197 B2 | 11/2011 | Sheppard |
| 8,094,009 B2 | 1/2012 | Allen et al. |
| 8,099,074 B2 | 1/2012 | Ebner |
| 8,109,921 B2 | 2/2012 | Estes et al. |
| 8,115,600 B2 | 2/2012 | Stevenson et al. |
| 8,130,095 B2 | 3/2012 | Allen et al. |
| 8,147,446 B2 | 4/2012 | Yodfat et al. |
| 8,206,350 B2 | 6/2012 | Mann et al. |
| 8,211,364 B2 | 7/2012 | Drucker et al. |
| 8,221,359 B2 | 7/2012 | Kristensen et al. |
| 8,236,242 B2 | 8/2012 | Drucker et al. |
| 8,250,483 B2 | 8/2012 | Blomquist |
| 8,257,652 B2 | 9/2012 | Drucker et al. |
| 8,257,653 B2 | 9/2012 | Drucker et al. |
| 8,267,921 B2 | 9/2012 | Yodfat et al. |
| 8,282,627 B2 | 10/2012 | Shelton et al. |
| 8,285,328 B2 | 10/2012 | Caffey et al. |
| 8,287,495 B2 | 10/2012 | Michaud et al. |
| 8,290,562 B2 | 10/2012 | Goode, Jr. et al. |
| 8,310,415 B2 | 11/2012 | McLaughlin et al. |
| 8,323,188 B2 | 12/2012 | Tran |
| 8,332,008 B2 | 12/2012 | Goode et al. |
| 8,344,847 B2 | 1/2013 | Moberg et al. |
| 8,346,399 B2 | 1/2013 | Blomquist |
| 8,369,919 B2 | 2/2013 | Kamath et al. |
| 8,377,031 B2 | 2/2013 | Hayter et al. |
| 8,390,244 B2 | 3/2013 | Wooley et al. |
| 8,395,581 B2 | 3/2013 | Gråskov et al. |
| 8,401,194 B2 | 3/2013 | Nierzwick et al. |
| 8,414,563 B2 | 4/2013 | Kamen et al. |
| 8,449,524 B2 | 5/2013 | Braig et al. |
| 8,451,230 B2 | 5/2013 | Celentano et al. |
| 8,454,557 B1 | 6/2013 | Qi et al. |
| 8,460,231 B2 | 6/2013 | Brauker et al. |
| 8,472,913 B2 | 6/2013 | Ebner |
| 8,573,027 B2 | 11/2013 | Rosinko et al. |
| 8,579,853 B2 | 11/2013 | Reggiardo et al. |
| 8,601,465 B2 | 12/2013 | Bernstein |
| 8,852,152 B2 | 10/2014 | Tverskoy |
| 8,868,794 B2 | 10/2014 | Masoud |
| 8,903,350 B2 | 12/2014 | Ebner |
| 8,938,306 B2 | 1/2015 | Lebel |
| 8,986,253 B2 | 3/2015 | DiPerna |
| 8,992,475 B2 | 3/2015 | Mann |
| 9,132,227 B2 | 9/2015 | Bryant, Jr. |
| 9,238,100 B2 | 1/2016 | Kruse et al. |
| 9,259,531 B2 | 2/2016 | Kamen |
| 9,335,910 B2 | 5/2016 | Farnan et al. |
| 9,474,856 B2 | 10/2016 | Blomquist |
| 9,486,571 B2 | 11/2016 | Rosinko |
| 9,565,718 B2 | 2/2017 | Swanson |
| 9,715,327 B2 | 7/2017 | Rosinko et al. |
| 9,737,656 B2 | 8/2017 | Rosinko |
| 2001/0027791 A1 | 10/2001 | Wallace et al. |
| 2002/0029776 A1 | 3/2002 | Blomquist |
| 2002/0078393 A1 | 6/2002 | Parker |
| 2002/0183693 A1 | 12/2002 | Peterson et al. |
| 2003/0065308 A1 | 4/2003 | Lebel et al. |
| 2003/0163088 A1 | 8/2003 | Blomquist |
| 2003/0163223 A1 | 8/2003 | Blomquist |
| 2003/0163789 A1 | 8/2003 | Blomquist |
| 2003/0199378 A1 | 10/2003 | Saviano |
| 2003/0212364 A1 | 11/2003 | Mann et al. |
| 2004/0073095 A1 | 4/2004 | Causey et al. |
| 2004/0193090 A1 | 9/2004 | Lebel et al. |
| 2004/0227737 A1 | 11/2004 | Novak et al. |
| 2005/0022274 A1 | 1/2005 | Campbell et al. |
| 2005/0143864 A1 | 6/2005 | Blomquist |
| 2005/0160084 A1 | 7/2005 | Barrett |
| 2005/0171513 A1 | 8/2005 | Mann et al. |
| 2006/0073891 A1 | 4/2006 | Holt |
| 2006/0173444 A1 | 8/2006 | Choy et al. |
| 2006/0195064 A1 | 8/2006 | Plahey et al. |
| 2006/0229557 A1 | 10/2006 | Fathallah et al. |
| 2007/0093786 A1 | 4/2007 | Goldsmith et al. |
| 2007/0118405 A1 | 5/2007 | Campbell et al. |
| 2007/0156033 A1 | 7/2007 | Causey et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |
| 2007/0287985 A1 | 12/2007 | Estes et al. |
| 2008/0033357 A1 | 2/2008 | Mann et al. |
| 2008/0065007 A1 | 3/2008 | Peterson et al. |
| 2008/0065016 A1 | 3/2008 | Peterson et al. |
| 2008/0119705 A1 | 5/2008 | Patel et al. |
| 2008/0122595 A1 | 5/2008 | Yamamichi et al. |
| 2008/0147004 A1 | 6/2008 | Mann et al. |
| 2008/0147050 A1 | 6/2008 | Mann et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0287922 A1 | 11/2008 | Panduro |
| 2009/0018495 A1 | 1/2009 | Panduro |
| 2009/0037020 A1 | 2/2009 | Brown |
| 2009/0067989 A1 | 3/2009 | Estes et al. |
| 2009/0069745 A1 | 3/2009 | Estes et al. |
| 2009/0082728 A1 | 3/2009 | Bikovsky |
| 2009/0085768 A1 | 4/2009 | Patel et al. |
| 2009/0101549 A1 | 4/2009 | Kamen et al. |
| 2009/0107335 A1 | 4/2009 | Wilt et al. |
| 2009/0108016 A1 | 4/2009 | Brown et al. |
| 2009/0156990 A1 | 6/2009 | Wenger et al. |
| 2009/0167717 A1 | 7/2009 | Wang et al. |
| 2009/0192724 A1 | 7/2009 | Brauker et al. |
| 2009/0212966 A1 | 8/2009 | Panduro |
| 2009/0221890 A1 | 9/2009 | Saffer et al. |
| 2009/0227888 A1 | 9/2009 | Saimi et al. |
| 2009/0254037 A1 | 10/2009 | Bryant, Jr. et al. |
| 2009/0270833 A1 | 10/2009 | DeBelser et al. |
| 2009/0289916 A1 | 11/2009 | Dai |
| 2010/0069890 A1 | 3/2010 | Gräskov et al. |
| 2010/0107103 A1 | 4/2010 | Wallaert et al. |
| 2010/0121169 A1 | 5/2010 | Petisce et al. |
| 2010/0134305 A1 | 6/2010 | Lu et al. |
| 2010/0145262 A1 | 6/2010 | Bengtsson et al. |
| 2010/0152674 A1 | 6/2010 | Kavazov et al. |
| 2010/0168543 A1 | 7/2010 | Kamath et al. |
| 2010/0179402 A1 | 7/2010 | Goode, Jr. et al. |
| 2010/0185142 A1 | 7/2010 | Kamen et al. |
| 2010/0185175 A1 | 7/2010 | Kamen et al. |
| 2010/0198183 A1 | 8/2010 | Lanigan et al. |
| 2010/0222735 A1 | 9/2010 | Plahey et al. |
| 2010/0228186 A1 | 9/2010 | Estes et al. |
| 2010/0261987 A1 | 10/2010 | Kamath et al. |
| 2010/0292556 A1 | 11/2010 | Golden |
| 2010/0292634 A1 | 11/2010 | Kircher, Jr. et al. |
| 2010/0312082 A1 | 12/2010 | Batman et al. |
| 2010/0331824 A1 | 12/2010 | Moberg et al. |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0030845 A1 | 2/2011 | Chong et al. |
| 2011/0040247 A1 | 2/2011 | Mandro et al. |

(56) References Cited

U.S. PATENT DOCUMENTS

| | | |
|---|---|---|
| 2011/0047499 A1 | 2/2011 | Mandro et al. |
| 2011/0053121 A1 | 3/2011 | Heaton |
| 2011/0071465 A1 | 3/2011 | Wang et al. |
| 2011/0082439 A1 | 4/2011 | Wenger et al. |
| 2011/0092894 A1 | 4/2011 | McGill et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0106318 A1 | 5/2011 | Ledford |
| 2011/0119087 A1 | 5/2011 | Drucker et al. |
| 2011/0125085 A1 | 5/2011 | McGill et al. |
| 2011/0125095 A1 | 5/2011 | Lebel et al. |
| 2011/0125530 A1 | 5/2011 | Drucker et al. |
| 2011/0126188 A1 | 5/2011 | Bernstein et al. |
| 2011/0133946 A1 | 6/2011 | Kopp et al. |
| 2011/0137239 A1 | 6/2011 | DeBelser et al. |
| 2011/0144586 A1 | 6/2011 | Michaud et al. |
| 2011/0152770 A1 | 6/2011 | DiPerna et al. |
| 2011/0178461 A1 | 7/2011 | Chong et al. |
| 2011/0184264 A1 | 7/2011 | Galasso et al. |
| 2011/0190614 A1 | 8/2011 | Brister et al. |
| 2011/0190694 A1 | 8/2011 | Lanier, Jr. et al. |
| 2011/0196289 A1 | 8/2011 | Plahey et al. |
| 2011/0208123 A1 | 8/2011 | Gray et al. |
| 2011/0256024 A1 | 10/2011 | Cole et al. |
| 2011/0257895 A1 | 10/2011 | Brauker et al. |
| 2012/0030610 A1 | 2/2012 | DiPerna et al. |
| 2012/0041415 A1 | 2/2012 | Estes et al. |
| 2012/0059353 A1 | 3/2012 | Kovatchev et al. |
| 2012/0084728 A1 | 4/2012 | Huang et al. |
| 2012/0095315 A1 | 4/2012 | Tenbarge et al. |
| 2012/0109100 A1 | 5/2012 | Estes et al. |
| 2012/0130204 A1 | 5/2012 | Basta et al. |
| 2012/0185267 A1 | 7/2012 | Kamen et al. |
| 2012/0203178 A1 | 8/2012 | Tverskoy |
| 2012/0232520 A1 | 9/2012 | Sloan et al. |
| 2013/0053816 A1 | 2/2013 | DiPerna et al. |
| 2013/0172710 A1 | 7/2013 | Mears et al. |
| 2013/0191770 A1 | 7/2013 | Bartz et al. |
| 2013/0283196 A1 | 10/2013 | Farnan et al. |
| 2013/0298024 A1 | 11/2013 | Rhee et al. |
| 2013/0332874 A1 | 12/2013 | Rosinko et al. |
| 2013/0345625 A1 | 12/2013 | Causey, III |
| 2014/0012511 A1 | 1/2014 | Mensinger et al. |
| 2014/0054883 A1 | 2/2014 | Lanigan et al. |
| 2014/0180711 A1 | 6/2014 | Kamen et al. |
| 2014/0276531 A1 | 9/2014 | Walsh |
| 2014/0323961 A1 | 10/2014 | Blomquist et al. |
| 2015/0072613 A1 | 3/2015 | Swanson |
| 2015/0182694 A1 | 7/2015 | Rosinko |
| 2015/0182695 A1 | 7/2015 | Rosinko |
| 2015/0217044 A1 | 8/2015 | Blomquist |
| 2016/0121047 A1 | 5/2016 | Kruse et al. |
| 2016/0199571 A1 | 7/2016 | Rosinko et al. |
| 2016/0271325 A1 | 9/2016 | Farnan et al. |
| 2017/0043085 A1 | 2/2017 | Rosinko |
| 2017/0056590 A1 | 3/2017 | DiPerna et al. |
| 2017/0300206 A1 | 10/2017 | Rosinko et al. |
| 2018/0361060 A9 | 12/2018 | Rosinko |

FOREIGN PATENT DOCUMENTS

| | | |
|---|---|---|
| EP | 2079011 A1 | 7/2009 |
| WO | WO 9524229 A2 | 9/1995 |
| WO | WO 0018449 A2 | 4/2000 |
| WO | WO 03008014 | 1/2003 |
| WO | WO 2008/127694 A1 | 10/2008 |
| WO | WO 2009/032399 A1 | 3/2009 |
| WO | WO 2009/032400 A1 | 3/2009 |
| WO | WO 2011/005633 A2 | 1/2011 |

OTHER PUBLICATIONS

Search Report dated Nov. 25, 2015 for EP Application No. 13781696.3, 8 pages.
Search Report and Written Opinion dated Jul. 29, 2013 for PCT Application No. PCT/US-2013/037616 filed Apr. 22, 2013, 10 pages.
Written Opinion dated Oct. 28, 2014 for PCT Application No. PCT/US-2013/037616 filed Apr. 22, 2013, 6 pages.
Search Report dated Jun. 6, 2017 for EP Application No. 13800236.5, 9 pages.
Search Report dated Sep. 4, 2013 for PCT Application No. PCT/US-2013/0044329 filed Jun. 13, 2013, 13 pages.
IPRP dated Dec. 9, 2014 for PCT Application No. PCT/US2013/0044329, 9 pages.
Examination Report dated Jan. 3, 2017 for EP Application No. 13781696.3, 6 pages.
PCT Search Report dated Sep. 4, 2013 for PCT Application No. PCT/US2013/044329 filed Jun. 13, 2013, 13 pages.
Introduction to Windows in DOC. Publisher: Imperial College London. Publication date: Feb. 28, 2011. URL: http://web.archive.org/web/20110228233235/https.//www.doc.ic.ac.uk/csg-old/window/intro.html, 7 pages.
Application and File History for U.S. Appl. No. 13/801,274, filed Mar. 13, 2013, inventor Farnan et al.
Application and File History for U.S. Appl. No. 13/801,230, filed Mar. 13, 2013, inventor Rosinko et al.
Application and File History for U.S. Appl. No. 15/149,559, filed May 9, 2016, inventor Farnan et al.
Search Report dated Jun. 24, 2019 for EP Application No. 18211743.2, 11 pages.

702

PREVENTING INADVERTENT CHANGES IN AMBULATORY MEDICAL DEVICES

RELATED APPLICATIONS

This application us a continuation of application Ser. No. 13/801,230 filed Mar. 13, 2013, which claims the benefit of U.S. Provisional Application No. 61/656,997 filed Jun. 7, 2012, each of which is incorporated herein in its entirety by reference.

BACKGROUND

Portable ambulatory medical devices have proved useful for treating patients with medical conditions that require continuous monitoring and/or treatment. One example of such a portable ambulatory medical device is a device that involves the delivery of fluids. There are many applications in academic, industrial, and medical fields, as well as others, that involve devices capable of accurately and controllably delivering fluids, including liquids and gases, that have a beneficial effect when administered in known and controlled quantities. This is particularly true in the medical field, where treatments for many of patients include the administration of a known amount of a substance at predetermined intervals. For example, the treatment of diabetes involves just such a regimented dosage of medicaments such as insulin. In addition, diabetes is one of a few medical indications wherein patients routinely administer the medicament to themselves by a subcutaneous modality, such as a hypodermic syringe injection or by an ambulatory infusion pump. As such, providing a patient with the means to safely, reliably, and comfortably administer required doses of medication such as, e.g., insulin, may be particularly important in order to facilitate patient compliance and accurate treatment of the condition.

Ambulatory insulin infusion pumps have been developed for the administration of insulin for those diagnosed with both type I and type II diabetes. Ambulatory insulin pumps are medical infusion devices used for the administration of insulin in the treatment of diabetes, and offer an alternative to multiple daily injections of insulin by an insulin syringe or an insulin pen. They also allow for continuous insulin therapy. In addition, some ambulatory insulin infusion devices can include data collection and storage mechanisms, which allow a diabetic person and/or a doctor to easily monitor and adjust insulin intake. The infusion device may be powered by a rechargeable battery that requires periodic recharging.

Some ambulatory medical devices include a touchscreen on which symbols may be displayed and from which inputs may be received for operation of the device. Other input mechanisms involve keyboards or hardware switches. In general, a series of display screens or windows are shown on a device display or on the device touchscreen, showing alphanumeric text and symbols, and providing menu screens through which the user can control operation of the device. User interaction, such as by touching the alphanumeric text and symbols, provides user input and facilitates navigation through the menu screens and selection of the device functions.

The phenomenon of unintended, inadvertent activation of portable devices is not an uncommon occurrence. Telephone calls accidentally placed via a mobile telephone through inadvertent activation have become a fact of modern life. Such accidental calls can be annoying and troublesome for a mobile telephone. In the case of a portable ambulatory medical device, such accidental activation can have serious consequences. In fact, in the case of portable ambulatory medical devices, any changes at all that are unintended or inadvertent may be problematic and even dangerous. For example, an untimely delivery of insulin, or delivery of an unexpectedly changed amount of insulin, or the absence of an expected dose, can have extremely deleterious results, and may even be dangerous to the user. User safety would be improved with a reduction in the likelihood of an accidental or unintended activation or deactivation of a portable ambulatory medical device.

SUMMARY

Disclosed herein are portable ambulatory medical devices and methods of operation that provide a reduced likelihood of inadvertent change in device operation. A device includes an active mode in which the device receives a user input at an input interface of the device and provides the received user input to a processor of the device. The active mode can be terminated and the device operated in a safe mode, in which the received user input is not provided to the processor and/or one or more device function is disabled, in response to determining that the received user input was received in an out of bounds region of the input interface. The safe mode is terminated in response to receiving a predetermined user input comprising an activation input. In some embodiments, the activation input can comprise selection of a wake display button or icon of the user interface, or may comprise a predetermined sequence of selected buttons or icons of the user interface.

In one embodiment, the activation input may be modified to require a timed pattern to wake the touchscreen. The pattern would require two or more presses that would be delivered in specified time windows, and if presses where detected outside of these windows, the sequence would be aborted.

In some embodiments, the portable device may include a user interface with control features such as buttons, switches or icons to control pumping and other functions, and the portable device may include a touchscreen on which are displayed alphanumeric text, symbols, menu screens, data, alerts, and other information. The device may show one or more screens or windows on the touchscreen through which device control inputs are received. For each device screen display, one or more regions of the display, and/or one or more buttons or switches, will be considered out of bounds for any intended control input. During an active mode of the device, when control inputs are received, any user interaction with an out of bounds region can cause the active mode to be suspended and the device will be in a safe mode of operation in which at least one of the device components is not operated. The device will remain in the safe mode until it receives an activation input before permitting continued active operation. The activation input may comprise a sequence of multiple inputs from the user via the touchscreen or a group of multiple inputs provided simultaneously, such as multiple simultaneous button presses. Failure to receive the activation input will result in the device remaining in the safe mode. The activation input may require the user to comply with activation sequence parameters as to both multiple symbol interactions and time between the multiple interactions. Requiring the predetermined activation sequence before resuming normal operation reduces the likelihood of accidental or unintended activation of the portable ambulatory medical device and improves user safety.

Other features and advantages of the present invention should be apparent from the following description of preferred embodiments that illustrate, by way of example, the principles of the invention.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Disclosed herein are embodiments directed to a portable medical device having an interactive display screen, such as a touch screen, for control by the user, and having a connecting tube with an infusion port for administering medication to a patient.

Figure 1:
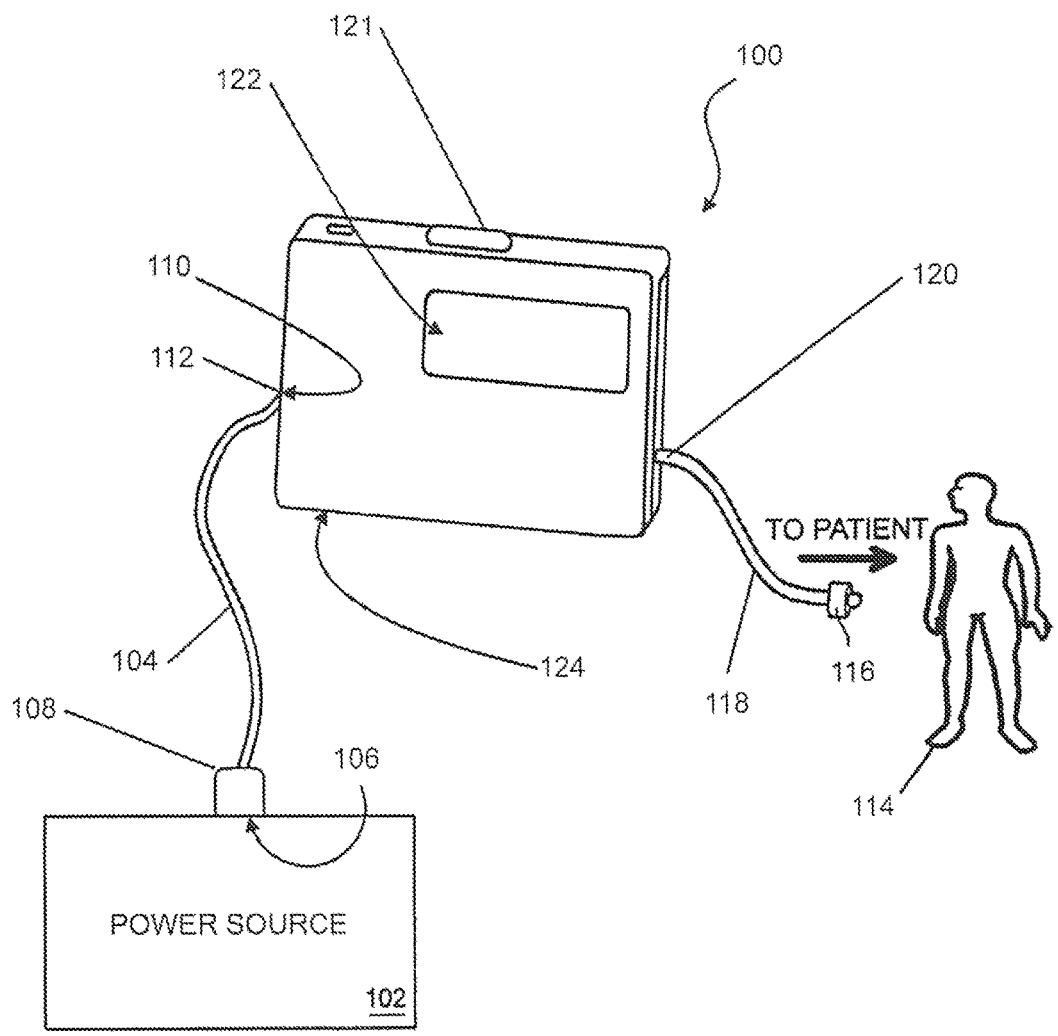
FIG. 1 depicts a portable device according to an embodiment of the present invention that is coupled to a patient for infusing medication thereto.

FIG. 1 shows an electrically-powered portable device 100 that is coupled to a host power source 102, such as a desktop or laptop computer, through a cable 104. The cable may comprise, for example, a coupling through which both data and electrical energy are received at the portable device 100. Examples of such combined power and data cables include a Universal Serial Bus (USB) connection, an IEEE 1499 connection, a "THUNDERBOLT" connection (i.e., from Apple, Inc., of Cupertino, Calif., USA), PCI Express, eSATA and Ethernet. The host power source 102 is a source of electrical energy and can be any type of computing device that includes a port 106 that receives a connector 108 of the cable 104. The port of the host computing device may comprise, for example, a USB port, or IEEE 1499 port, or port for THUNDERBOLT, PCI Express, eSATA or Ethernet. A compatible connector port 110 of the portable device 100 is coupled to the cable 104 at an opposite end 112 of the cable. In a USB implementation, for example, the cable 104 is a USB cable and associated connections and ports may support one or more of USB version 1.1, 2.0, or 3.0 data transfer speeds.

The portable device 100 may be coupled to a patient 114 via an infusion port 116 and a connecting tube or cannula 118. The connecting tube is coupled to the portable device 100 at a fluid dispending port 120. The portable device may include control features, such as buttons or switches 121 to receive user input and control pumping and other features, and may include a display screen 122 on which are displayed messages and alerts. The display 122 may comprise, for example, a touchscreen on which user inputs may be received. A housing 124 of the portable device encloses internal components, such as fluid reservoirs, electrical components, battery, and the like. The portable device 100 illustrated in FIG. 1 comprises a portable medical device of the type worn by a patient 114 such that insulin fluid is delivered via the connecting tube 118 and the fluid dispensing port 120 by a delivery mechanism. Exemplary ambulatory medical devices and features include those, e.g., disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495. Each of the aforementioned documents is hereby incorporated herein by reference in its entirety.

The portable device 100 can be coupled to a host power source such as a desktop or laptop computer, through a cable connected to the connector port 110. The cable may comprise, for example, a coupling through which both data and electrical energy are received at the portable device 100. Examples of such combined power and data cables include a Universal Serial Bus (USB) connection, an IEEE 1499 (FireWire) connection, a "THUNDERBOLT" connection (from Apple, Inc. of Cupertino, Calif., USA), PCI Express, eSATA and Ethernet.

The device 100 may also include a capability to operatively couple to one or more other devices via a wired or wireless (e.g., infrared, electronic, optical, etc.) link, locally or via a network, such as, e.g., a portable or non-portable medical device, a control unit, external monitor or display, a personal laptop, tablet or mainframe computer, or mobile communication device such as a smartphone or personal digital assistant (PDA). Such other devices may control or be controlled by device 100 and/or may otherwise communicate for the transfer of data including device parameters between or among device 100 and other device(s) for analysis of data (e.g., user data for physician review, device diagnostic data for troubleshooting or repair), programming, or other uses.

The portable device 100 may include control features such as buttons, panels, screens, and/or switches to control the device, or any combination of such control features. For example, the portable device 100 illustrated in FIG. 1 shows a touchscreen 122 on which can be displayed alphanumeric text, symbols, menu screens, data, alerts and the like for receiving control input. The portable device may include a processor with memory, wherein the processor executes program instructions to provide an operating system that supports programs that execute and provide the specified features. The touchscreen 122 may be interactive, wherein user input may be received such as by pressing the outer surface of the touchscreen. The touchscreen 122 may be configured to display menu screens or pages that allow the user to input data fields, e.g., select device parameters, so as to allow the program to produce a suggested delivery amount, rate, profile, and/or the like in an intuitive, manipulable, and/or graphic representation, thereby allowing the user to interact with the screen to shape the characteristic/form of the delivery amount, rate, and/or graphic delivery profile, e.g., by manipulating the delivery estimate or pattern displayed on the screen to effectuate the actual delivery.

Device parameters provided by the portable infusion device may be presented on the display screen 122 as any number of objects, including one or more numeric and/or alphanumeric values, a range, a value or range that is presented in the form of a drop-down menu, a toggle that can be adjusted by the user, a graphical representation (e.g., icon) or an animated graphic. For instance, in certain embodiments, the value is a range of values that are presented on a screen of the display as a toggle, wherein the toggle may be adjusted upwards or downwards by the user swiping a finger over the screen to select the appropriate value range, e.g. appropriate range of amounts of medicament such as insulin to be delivered and/or the appropriate rate, time, or interval of medicament delivery. In certain instances, the values presented in the range may be adjusted by the processor (illustrated in FIG. 2). Other device parameters will be readily apparent to those skilled in the art.

The type of touch screen 122 may vary as desired to be useful for a particular application, such as LCD displays, LED displays, plasma displays, organic LED (OLED) displays, and the like. The touchscreen 122 may be implemented with a capacitance screen, a resistive screen, or other such display/input technology. The portable device 100 may additionally include a keyboard or other input device known in the art for data entry, which may be separate from the display.

Figure 2:
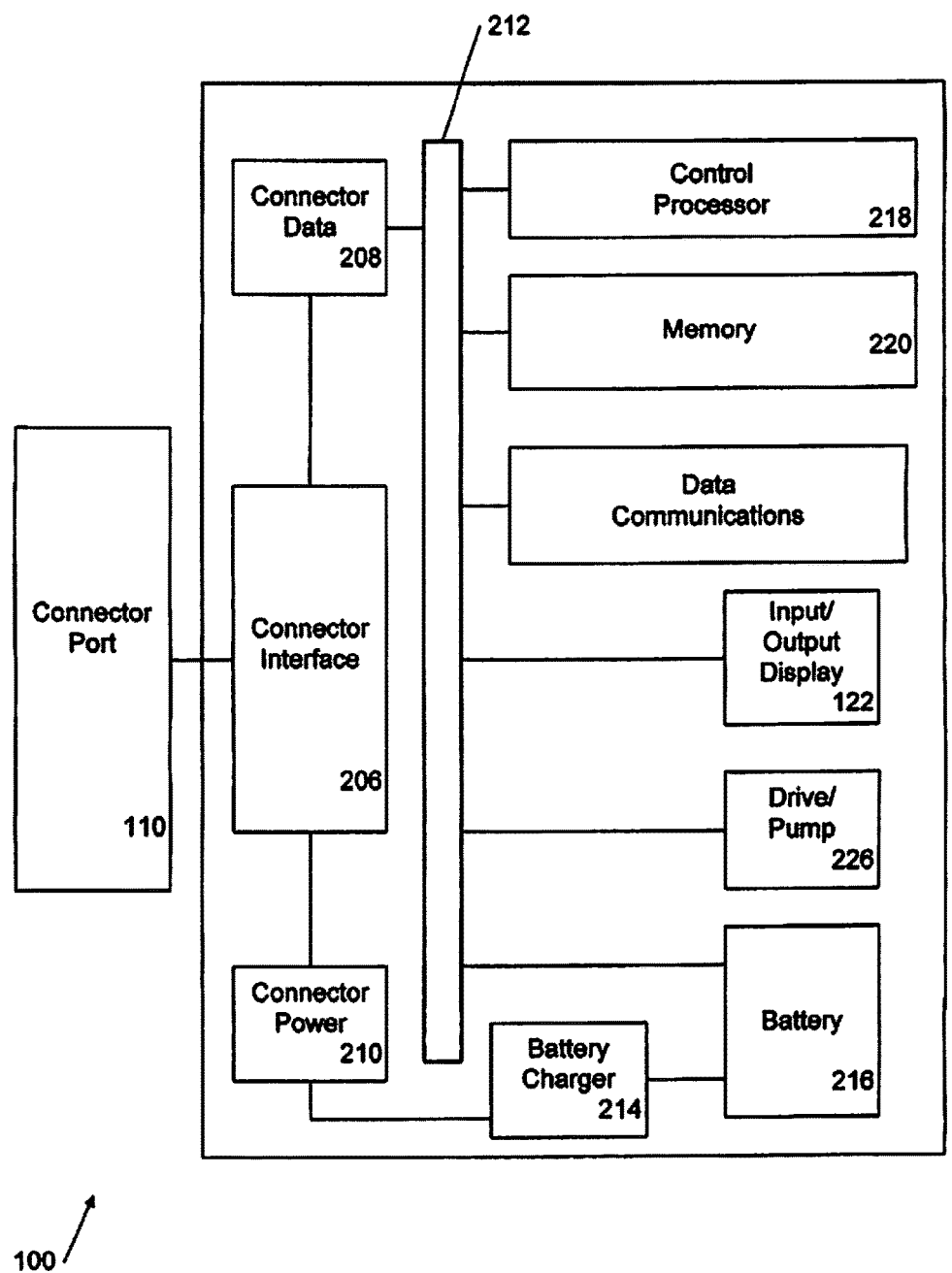
FIG. 2 is a block diagram of circuitry and components for the portable medical device illustrated in FIG. 1.

FIG. 2 shows a block diagram of some of the components within the portable device 100 of FIG. 1. The portable device 100 includes a power management system 202 that is connected to the connector port 110 that receives a combined data/power cable, such as the USB cable 104 illustrated in FIG. 1. That is, the cable 104 has the capability of simultaneously providing electrical energy for charging and data transmission for communications. A connector interface 206 supports data exchange and receives electrical power through the connector port 110, and controls a connector data element 208 and a connector power element 210. The device may be powered by battery power in place of or in addition to the connector interface. The connector interface 206 passes data communications from the connector port 110 through the connector data element 208 to a system bus 212. The connector interface 206 passes electrical power from the connector port 110 through the connector power element 210 to a battery charger 214, which in turn is coupled to a battery 216 and which recharges the battery. In one embodiment, he connector data element 208 is implemented in the FIG. 2 device with a USB Isolation Chip ADUM4160 product from Analog Devices, Inc. of Norwood, Mass., USA, and the connector power element 210 is implemented in the FIG. 2 device with a USB Power Isolation Chip LT3573 product from Linear Technology Corporation of Milpitas, Calif., USA. Those skilled in the art will be aware of alternative suitable devices.

A control processor 218 is connected to the system bus 212 and receives the data communications from the connector data element 208 for processing. The control processor controls operation of the various elements of the portable device 100 that are connected to the system bus. The control processor operates according to mode instructions that may be stored in device memory 220.

The portable device 100 operates under control of the processor 218 so as to include at least two modes of operation, comprising an active mode and a safe mode. The active mode is an operating mode in which multiple device components are operated. The safe mode is an operating mode in which at least one device component is deactivated and is not operated. For example, in the active mode, the touchscreen display 122 and the pump 226 may be operated, whereas, in the safe mode, the pump may be deactivated and not operated.

Figure 3:
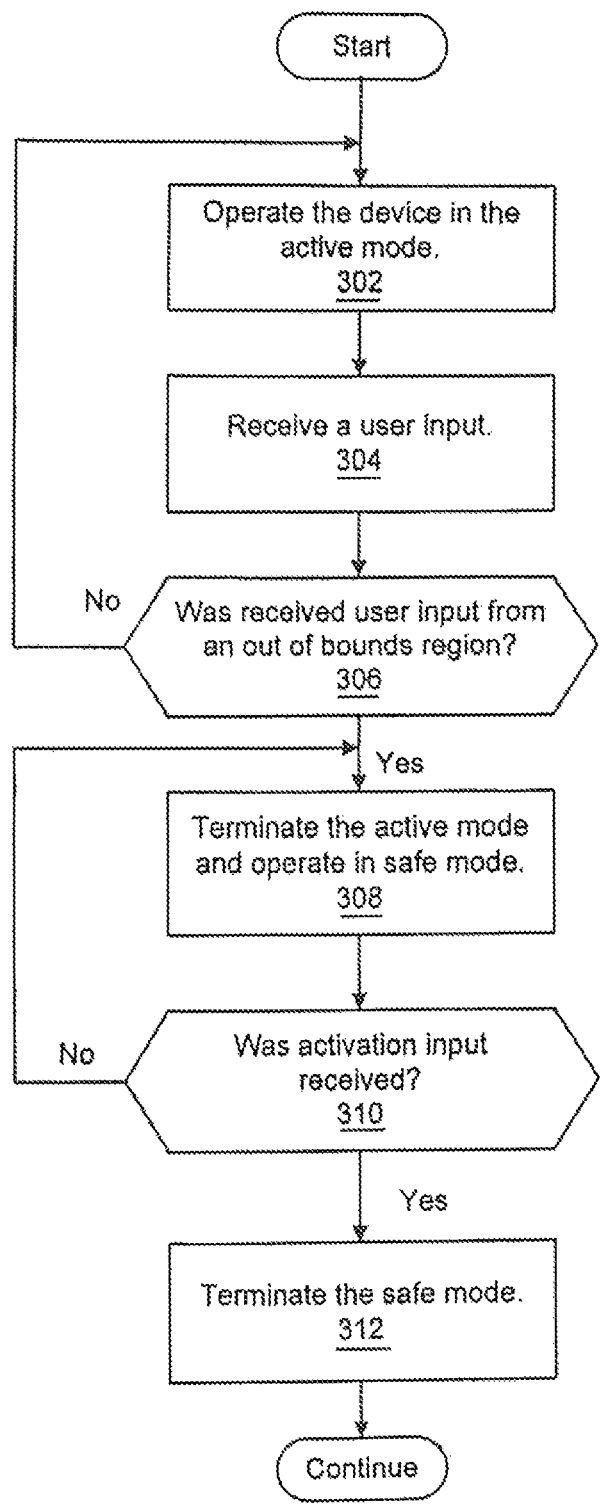
FIG. 3 is a flow diagram showing operations of the device in FIG. 1.
Figure 4:
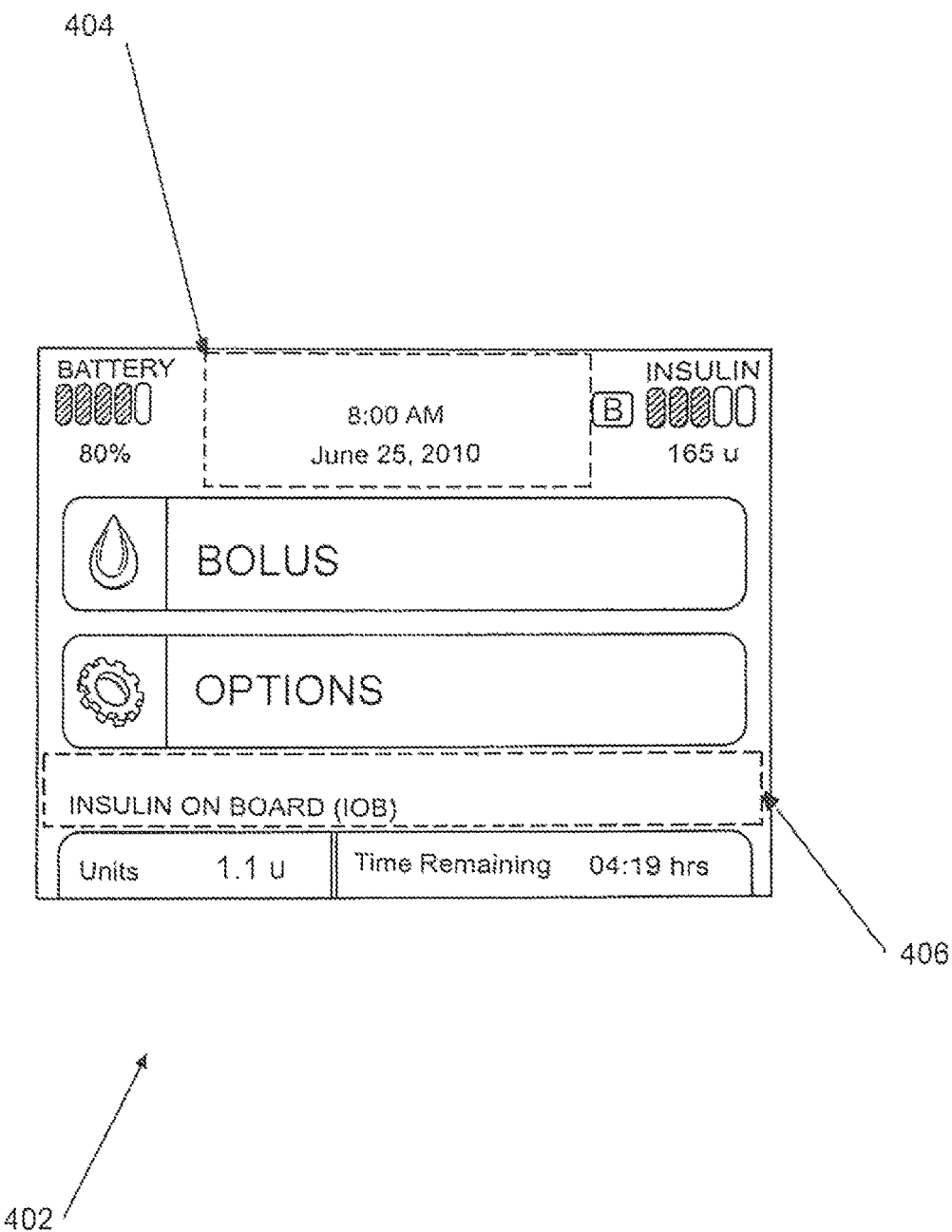
FIG. 4 depicts a display screen with a home screen display showing out-of-bounds regions according to an embodiment of the present invention.
Figure 5:
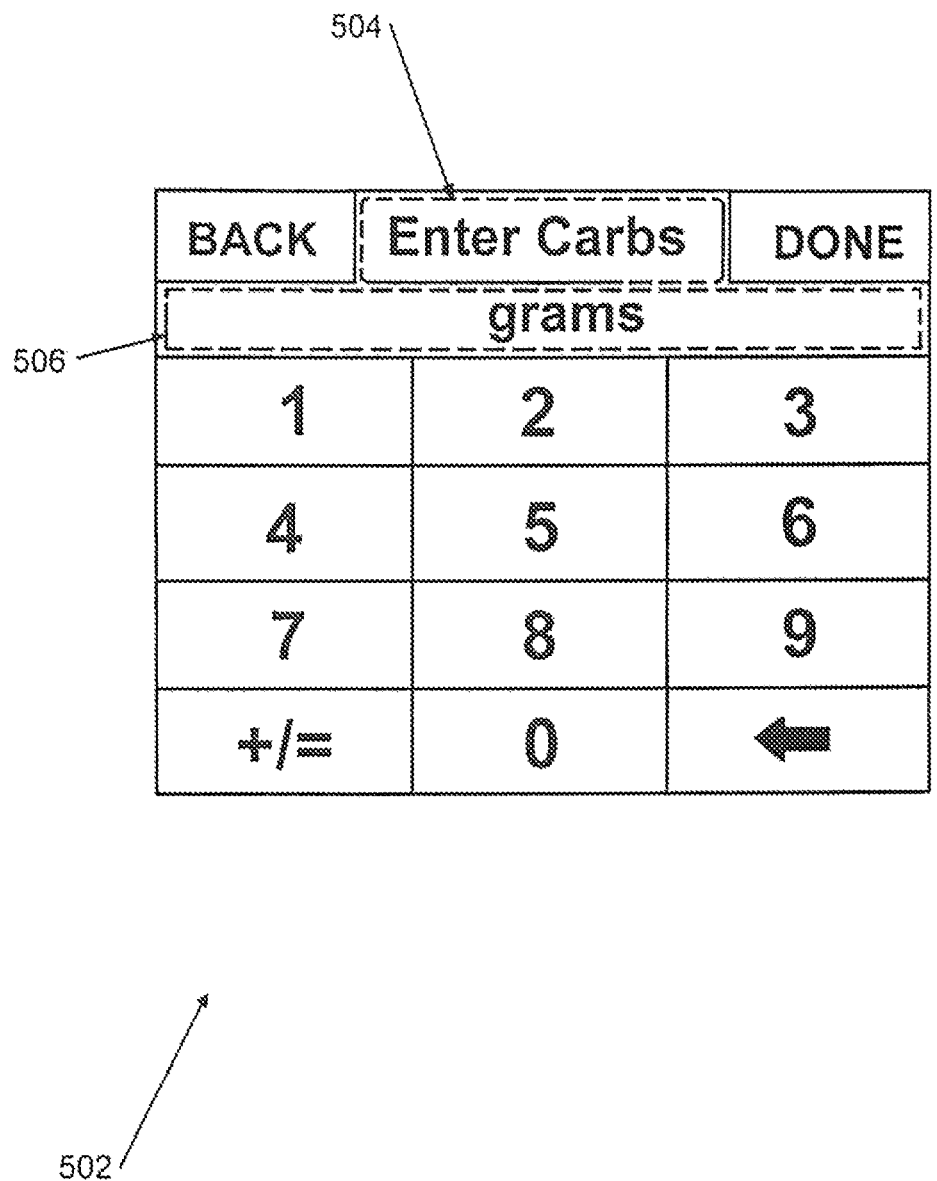
FIG. 5 depicts a display screen with a data entry screen display showing out-of-bounds regions according to an embodiment of the present invention.
Figure 6:
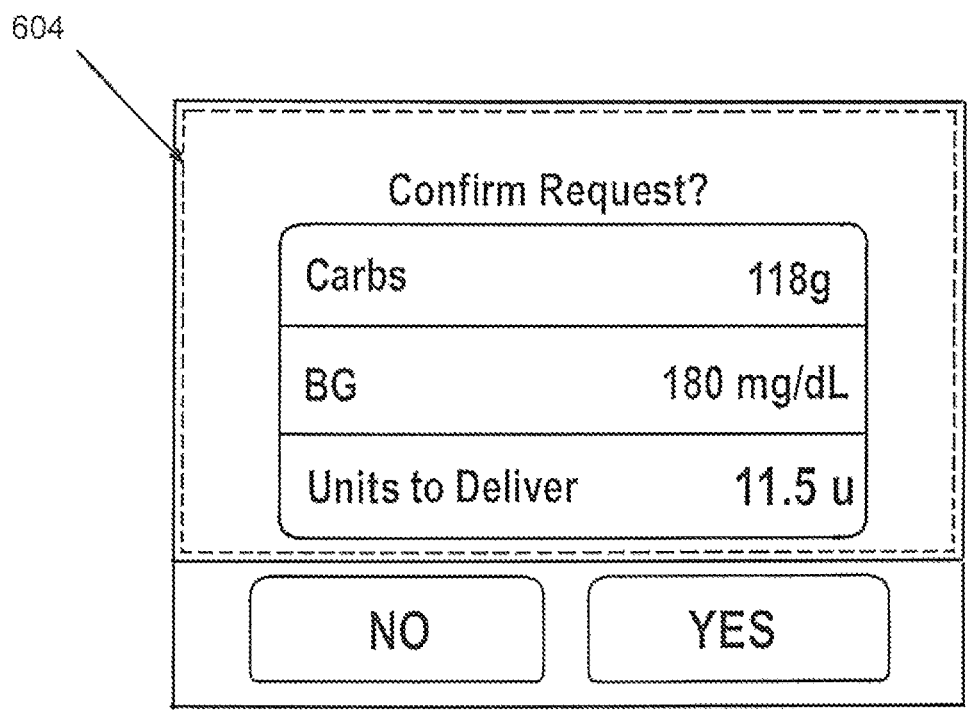
FIG. 6 depicts a display screen with a confirmation screen display showing an out-of-bounds region according to an embodiment of the present invention.

FIG. 3 is a flowchart that illustrates operation of the device. In the first operation, indicated by the flowchart box 302, the processor operates the device in the active mode, in which a user may enter input at the input interface of the device. At the next operation, at box 304, a user input is received at the input interface. The user input may comprise an intentional input at the device, such as a user interaction with the touchscreen, or the user input may comprise an accidental interaction with the touchscreen. The user input may optionally comprise making an affirmative action to place the device into safe mode. For example, the affirmative action may comprise pressing a physical button or switch on the device or on a smart phone that turns off the display. This option useful, for example, for placing the device in the safe mode prior to placing the device in a pocket or purse. In the next operation, indicated by the decision box 306, the device processor determines if the received user input was at an out of bounds region of the display. For each display screen during operation of the device, predetermined areas of the display screen will comprise an active area and other predetermined areas will comprise an out of bounds region. For example, FIGS. 4, 5, and 6 illustrate display screens with the respective predetermined out of bounds regions indicated. FIG. 4 shows a home screen display 402 with two rectangular out-of-bounds regions 404, 406 identified. FIG. 5 shows a data entry screen display 502 with two out-of-bounds regions 504, 506 identified. FIG. 6 shows confirmation screen display 602 with a relatively large rectangular out-of-bounds region 604 identified. Any single button input or predetermined plurality of inputs received in any of the out-of-bounds regions during a respective active operation while the corresponding screen is displayed will result in the device entering the safe mode.

Returning to the flow diagram of FIG. 3, if the input was at an out-of-bounds region, an affirmative outcome at box 306, then the processor proceeds to the operation of box 308, terminating the active mode of operation and initiating operation of the device in the safe mode. If the input was not received from an out of bounds region, a negative outcome at box 308, then the device continues to operate in the active mode and additional input may be received, as indicated by the return to operation at box 302. The processor will deactivate at least one component of the device while in the safe mode of operation. For example, the processor may deactivate the pump of the device while it is in the safe mode, to ensure that no accidental delivery of insulin is initiated. The processor may disable changes to settings in memory, to ensure that bolus settings and the like are not changed during the safe mode.

While in the safe mode of operation, the processor waits for an input comprising an activation input. If an activation input is received, an affirmative outcome at box 310, then the process terminates the safe mode of operation. Typically, the processor will return to the active mode of operation, but other modes may be initiated, as desired. For example, a power saving mode might be preferred. If no activation input is received, a negative outcome at box 310, then the processor maintains the device in the safe mode.

The activation input may comprise selection of a wake display button or icon of the user interface. Alternatively, the activation input may comprise predetermined sequence of selected buttons or icons of the user interface. For example, the sequence may comprise discrete selection of predetermined buttons on the touchscreen display. In another alternative, the predetermined sequence may comprise a sequence of predetermined button selections separated by predetermined amounts of time. For example, the predetermined sequence may involve button selections that are separated in time by no more than an activation time value.

The activation time value may have a value of, for example, no more than two seconds. If the time elapsed between any two display button selections is greater than two seconds, then the processor will consider the inputs to be random or accidental, and the processor will remain in the safe mode. In a further embodiment, the activation input can comprise a user swiping a touchscreen in a predetermined pattern or shape.

Figure 7:
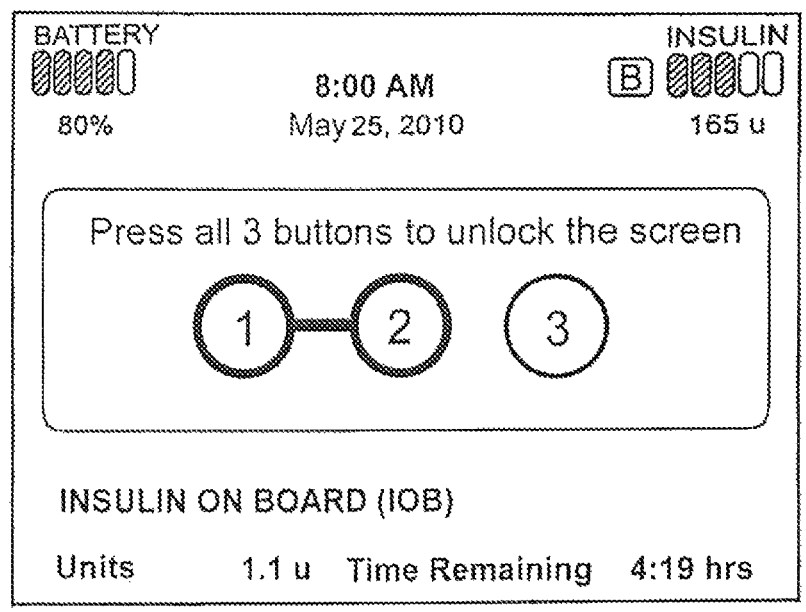
FIG. 7 depicts a display screen with an unlock screen display.

FIG. 7 shows an example of an unlock screen 702 that is displayed on the touchscreen of the device as part of the safe mode operation. That is, when the device enters the safe mode, the processor produces an unlock screen display and awaits the activation input from that screen. For example, in FIG. 7, the three buttons labeled "1", "2", and "3" must be pressed in proper (numerical) sequence, separated in time by no more than an activation time value.

In some embodiments, the safe mode can also be entered at the end of one or more predetermined sequences of user interaction with the pump, such as a sequence after which a user is likely to be finished interacting with a pump for a period of time. For example, after a user programs a bolus and executes a deliver command, the pump can automatically enter a safe mode in which the screen is locked. This would prevent the user from inadvertently cancelling or modifying the bolus or otherwise interacting with the device in an unintended fashion during the bolus delivery while, for example, placing the pump back against the user's body. Pump operation can therefore subsequently be modified during delivery of the bolus only by unlocking the screen as described above. In one embodiment, the pump can remain locked after the bolus is delivered and until the screen is unlocked.

Although the aforementioned description specifically describes a portable medical device for administering insulin to a patient, it should be understood that such a device is only one embodiment of the invention. The device can also include any portable device having a display and a processor. For example, the device can include a mobile computing device, such as a Smartphone. In one embodiment, such a mobile computing device can be used as a remote control to wirelessly control operations of medical devices as disclosed herein. Alternatively, medical devices as disclosed herein can be controlled remotely with a dedicated remote control specifically designed for use with the medical device.

The methods, systems, and devices discussed above are intended merely to be examples. Various embodiments may omit, substitute, or add various procedures or components as appropriate. For example, it should be appreciated that, in alternative embodiments, the methods may be performed in an order different from that described, and various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in this description to provide a thorough understanding of the embodiments. Nevertheless, it will be understood by one of ordinary skill in the art that the embodiments may be practiced without these specific details. For example, well-known circuits, processes, algorithms, structures, and techniques have been shown without unnecessary detail in order to avoid obscuring the embodiments. Further, the headings provided herein are intended merely to aid in the clarity of the descriptions of various embodiments, and should not be construed as limiting the scope of the invention or the functionality of any part of the invention. For example, certain methods or components may be implemented as part of other methods or components, even though they are described under different headings.

It is noted that embodiments may have been described as a process that is depicted as a flow diagram or block diagram. Although each diagram may describe the process as a sequential series of operations, many of the operations can be performed in parallel or concurrently. In addition, the order of the operations may be rearranged. A process may have additional steps not included in the figures. Each operation of a process is performed or executed by the processor of the device.

The description above has been provided in terms of presently preferred embodiments so that an understanding of the present invention can be conveyed. There are, however, many configurations and techniques for data management systems that were not specifically described herein, but with which the present invention is applicable. The present invention should therefore not be seen as limited to the particular embodiments described herein, but rather, it should be understood that the present invention has wide applicability with respect to data management generally. All modifications, variations, or equivalent arrangements and implementations that are within the scope of the attached claims should therefore be considered within the scope of the invention.

The invention claimed is:

1. A method for preventing inadvertent changes in operation of an ambulatory infusion pump, comprising:
presenting a user interface for control of an ambulatory infusion pump on a touchscreen display, the user interface configured to display at least one input screen and receive touch input from a user on the at least one screen;
presenting one or more active areas on the at least one input screen, the one or more active areas including one or more selectable objects configured to receive touch input from the user for programming and/or operation of the ambulatory infusion pump;
presenting one or more out of bounds regions on the at least one input screen, the one or more out of bounds regions defined as one or more areas of the input screen that are not the one or more selectable objects and as one or more areas at which touch input for programming and/or operation of the ambulatory infusion pump is not intended to be received;
identifying one or more touch inputs on one or more of the out of bounds regions on the at least one input screen while the ambulatory infusion pump is in an active mode during which touch input received via the one or more selectable objects is provided to a processor of the ambulatory infusion pump for programming and/or operation of the ambulatory infusion pump; and
placing the ambulatory infusion pump in a safe mode in response to the one or more touch inputs on the one or more of the out of bounds regions, wherein in the safe mode touch input received in the one or more selectable objects is not processed for programming and/or operation of the ambulatory infusion pump.

2. The method of claim 1, wherein presenting the user interface for control of the ambulatory infusion pump on the touchscreen display includes presenting the user interface on the ambulatory infusion pump.

3. The method of claim 1, wherein presenting the user interface for control of the ambulatory infusion pump on the touchscreen display includes presenting the user interface on a separate device from the ambulatory infusion pump.

4. The method of claim 3, wherein the separate device is a mobile computing device.

5. The method of claim 4, wherein the mobile computing device is a smartphone.

6. The method of claim 3, wherein the separate device is a remote control device specifically designed for use with the ambulatory infusion pump.

7. The method of claim 1, further comprising:
receiving a predetermined activation input via the touchscreen display while the ambulatory infusion pump is in the safe mode; and
terminating the safe mode and returning the ambulatory infusion pump to the active mode in response to the predetermined activation input.

8. The method of claim 7, wherein receiving a predetermined activation input includes receiving a predetermined sequence of selected icons on the touchscreen display.

9. The method of claim 7, further comprising displaying an unlock screen on the touchscreen display upon placing the ambulatory infusion pump in safe mode, and wherein the predetermined activation input is received via the unlock screen.

10. A method for preventing inadvertent changes in operation of an ambulatory infusion pump, comprising:
presenting a user interface for control of an ambulatory infusion pump on a touchscreen display, the user interface configured to display at least one input screen and receive touch input from a user on the at least one input screen;
providing one or more predetermined active areas and one or more predetermined out of bounds regions on the at least one input screen of the touschscreen display for control of the ambulatory infusion pump, the one or more active areas on the at least one input screen including one or more selectable objects configured to receive touch input from the user for programming and/or operation of the ambulatory infusion pump and the out of bounds regions on the at least one input screen defined as one or more areas that are not the one or more selectable objects and at which touch input for programming and/or operation of the ambulatory infusion pump is not intended to be received;
identifying one or more touch inputs on one or more of the out of bounds regions on the input screen while the ambulatory infusion pump is in an active mode; and
automatically disabling at least one function of the ambulatory infusion pump and placing the ambulatory infusion pump in a safe mode in response to the one or more touch inputs on the one or more of out of bounds regions, wherein in the safe mode touch input received in the one or more selectable objects is not processed for programming and/or operation of the ambulatory infusion pump.

11. The method of claim 10, wherein displaying of the at least one input screen on the touchscreen display includes displaying the input screen on the touchscreen display of the ambulatory infusion pump.

12. The method of claim 10, wherein displaying of the at least one input screen on the touchscreen display includes displaying the input screen on the touchscreen display of a separate device from the ambulatory infusion pump.

13. The method of claim 12, wherein the separate device is a mobile computing device.

14. The method of claim 13, wherein the mobile computing device is a smartphone.

15. The method of claim 12, wherein the separate device is a remote control device specifically designed for use with the ambulatory infusion pump.

16. The method of claim 10, further comprising:
receiving a predetermined activation input via the touchscreen display while the at least one function of the ambulatory infusion pump is disabled; and
enabling the at least one disabled function of the ambulatory infusion pump in response to the predetermined activation input.

17. The method of claim 16, wherein receiving a predetermined activation input includes receiving a predetermined sequence of selected icons on the touchscreen display.

18. The method of claim 16, further comprising displaying an unlock screen on the touchscreen display when the at least one device function is disabled, and wherein the predetermined activation input is received via the unlock screen.

* * * * *